United States Patent
Thomas et al.

(10) Patent No.: US 9,119,605 B2
(45) Date of Patent: Sep. 1, 2015

(54) SYNTHETIC POLYMER ADHESIVES AND METHODS FOR MAKING, USING AND DELIVERING THE SAME

(75) Inventors: Brian Thomas, Columbia City, IN (US); Donald Yakimicki, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 421 days.

(21) Appl. No.: 13/099,549

(22) Filed: May 3, 2011

(65) Prior Publication Data

US 2011/0276088 A1  Nov. 10, 2011

Related U.S. Application Data

(60) Provisional application No. 61/332,008, filed on May 6, 2010.

(51) Int. Cl.
| | |
|---|---|
| A61B 17/03 | (2006.01) |
| A61B 17/00 | (2006.01) |
| A61L 24/04 | (2006.01) |
| C09J 129/04 | (2006.01) |
| G09B 23/28 | (2006.01) |
| C08K 3/22 | (2006.01) |
| C08K 3/38 | (2006.01) |

(52) U.S. Cl.
CPC ......... *A61B 17/00491* (2013.01); *A61L 24/043* (2013.01); *C09J 129/04* (2013.01); *G09B 23/285* (2013.01); *A61B 2017/00495* (2013.01); *A61B 2017/00707* (2013.01); *C08K 3/22* (2013.01); *C08K 3/38* (2013.01)

(58) Field of Classification Search
CPC .............................. A61L 24/043; A61L 24/03
USPC .......................................................... 523/118
See application file for complete search history.

(56) References Cited

U.S. PATENT DOCUMENTS

| | | | |
|---|---|---|---|
| 4,424,291 A * | 1/1984 | Leake et al. .................... | 524/47 |
| 4,608,111 A | 8/1986 | Hume, III et al. | |
| 5,271,943 A | 12/1993 | Bogart et al. | |
| 6,596,267 B1 | 7/2003 | Hubbell et al. | |
| 6,673,285 B2 | 1/2004 | Ma | |
| 6,683,120 B2 | 1/2004 | Munro | |
| 7,029,688 B2 | 4/2006 | Hubbell et al. | |
| 7,303,759 B2 | 12/2007 | Mershon | |
| 7,531,000 B2 | 5/2009 | Hodorek | |
| 2004/0192811 A1* | 9/2004 | Skuratowicz .................. | 524/47 |
| 2005/0037038 A1 | 2/2005 | Gupta | |
| 2005/0124038 A1 | 6/2005 | Aguiar et al. | |

(Continued)

OTHER PUBLICATIONS

McCormick, F. et al., "Minced Articular Cartilage—Basic Science, Surgical Technique, and Clinical Application", Sports Med. Arthrosc. Rev., pp. 217-220, vol. 16, No. 4, (Dec. 2008).

(Continued)

*Primary Examiner* — Michael Pepitone
(74) *Attorney, Agent, or Firm* — Schwegman Lundberg & Woessner, P.A.

(57) ABSTRACT

A synthetic polymer based adhesive formulation that has properties substantially simulating selected properties of fibrin glue, and methods of making and using the same. The adhesive formulation includes a discrete acid solution and discrete base solution that when combined form a synthetic polymer based adhesive that substantially simulates selected properties of fibrin glue. The discrete acid solution includes a polymer and a cross-linking agent precursor. The discrete base solution includes a polymer and a base.

11 Claims, 1 Drawing Sheet

(56) References Cited

U.S. PATENT DOCUMENTS

| | | |
|---|---|---|
| 2005/0152882 A1 | 7/2005 | Kizer et al. |
| 2006/0008530 A1 | 1/2006 | Seyedin et al. |
| 2006/0105029 A1 | 5/2006 | Zhang et al. |
| 2006/0178749 A1 | 8/2006 | Pendleton et al. |
| 2006/0228391 A1 | 10/2006 | Seyedin et al. |
| 2006/0235541 A1 | 10/2006 | Hodorek |
| 2006/0235542 A1 | 10/2006 | Hodorek et al. |
| 2006/0263586 A1 * | 11/2006 | Lanthier et al. ............ 428/292.1 |
| 2007/0048251 A1 | 3/2007 | Arthur |
| 2007/0048337 A1 | 3/2007 | Arthur |
| 2007/0112428 A1 | 5/2007 | Lancial |
| 2007/0128152 A1 | 6/2007 | Hadba et al. |
| 2007/0128155 A1 | 6/2007 | Seyedin et al. |
| 2007/0179607 A1 | 8/2007 | Hodorek et al. |
| 2008/0195221 A1 | 8/2008 | Howald et al. |
| 2008/0253987 A1 | 10/2008 | Rehor et al. |
| 2009/0036995 A1 | 2/2009 | Lozier et al. |
| 2009/0143867 A1 | 6/2009 | Gage et al. |
| 2009/0317451 A1 | 12/2009 | Hauser |
| 2010/0120923 A1 | 5/2010 | Stewart et al. |

OTHER PUBLICATIONS

Schacht, E.H., "Polymer chemistry and hydrogel systems", Journal of Physics: Conference Series 3, pp. 22-28, (2004).

Hamilton, D. "Methods of Conserving Archeological Material from Underwater Sites", web printout from http://nautarch.tamu.edu/crl/conservationmanual/File2.htm, as of Mar. 25, 2010.

Zimmer web site printout "DeNovo NT Natural Tissue Graft" from http://www.zimmer.com/z/ct/op/global/action/1/id/10497/template/, as of Mar. 9, 2010.

Dr John Hyman web site printout "Medical News Pioneering Carthage Restoration Surgery—DeNovo NT" from http://www.drjonhyman.com/denovo.shtml, as of Mar. 9, 2010.

* cited by examiner

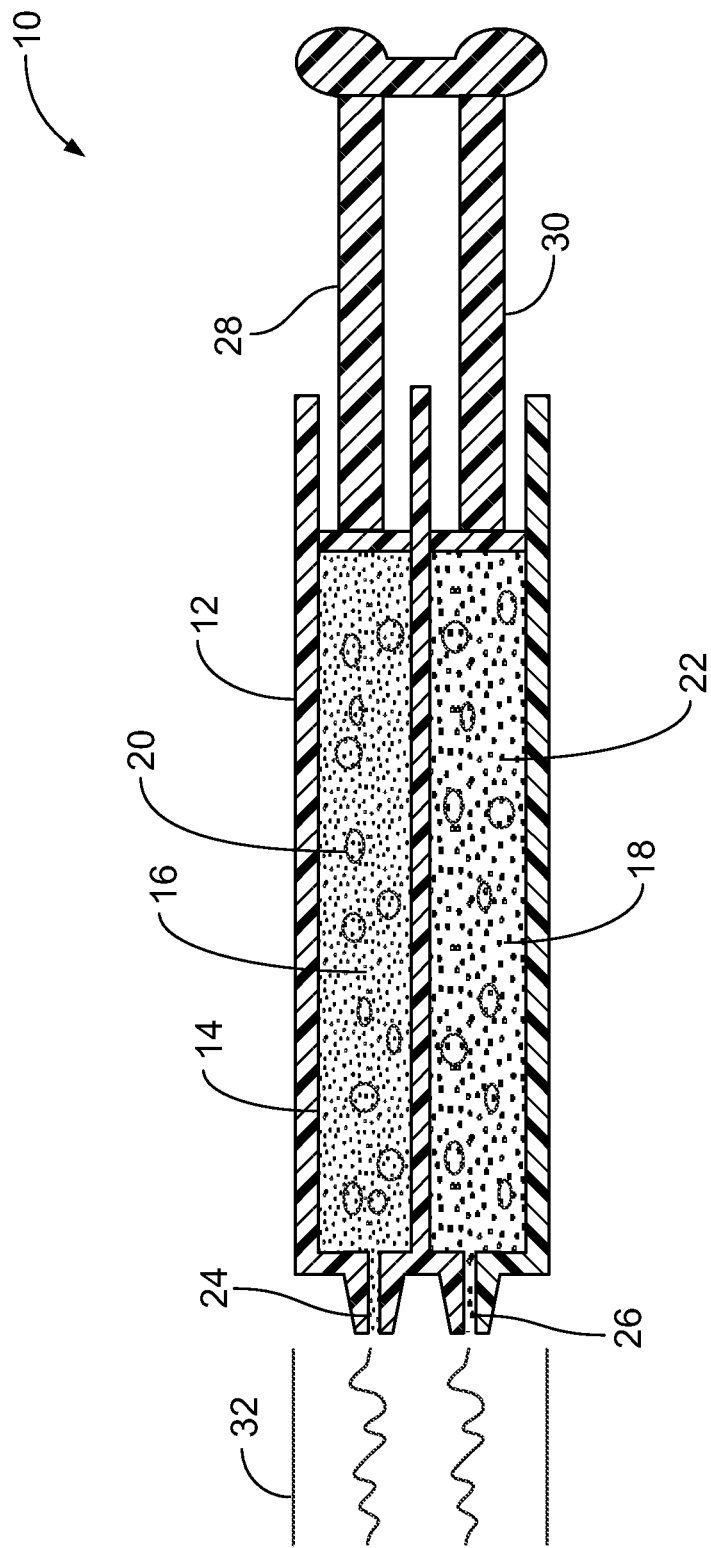

SYNTHETIC POLYMER ADHESIVES AND METHODS FOR MAKING, USING AND DELIVERING THE SAME

The present application claims the benefit of U.S. Provisional Patent Application Ser. No. 61/332,008, filed May 6, 2010, which is hereby incorporated by reference.

FIELD OF THE DISCLOSURE

The present disclosure relates to synthetic polymer adhesives and methods for making, using and delivering such adhesives. More particularly, the present disclosure relates to synthetic polymer adhesive formulations having properties that resemble the properties of fibrin glues, and even more particularly, to such synthetic polymer based adhesives that are relatively inexpensive to formulate and may be used in simulated medical procedures.

BACKGROUND

Fibrin glue is a tissue adhesive that is commonly used in many different medical procedures as a sealant, adhesive, biological carrier and/or hemostatic agent. For example, fibrin glues are used in cartilage repair and regeneration procedures, and in ophthalmic, cardiac and abdominal surgeries. Fibrin glue is formed from the mixing of at least two components, a fibrinogen component and a thrombin component.

There are several different methods for combining, dispensing and applying fibrin glue. For example, in one typical method, a double barreled syringe is used to combine and deliver the fibrinogen and thrombin components. The fibrinogen component is contained in one barrel of the syringe and the thrombin component is contained in the other barrel of the syringe. The fibrin glue is formed and applied by ejecting the components out of the barrels and combining them.

As part of their training, surgeons who perform procedures that involve the use of fibrin glues undergo simulated training in such procedures, including the delivery of fibrin glue. Because of the relatively high costs of fibrin glue (e.g., presently between five hundred to six hundred dollars for a single use), using actual fibrin glue in such simulated and training procedures can become quite costly, especially when the simulated procedure is repeated several times.

SUMMARY

The present disclosure is generally directed to synthetic polymer based adhesives that substantially resemble and/or simulate the characteristics and properties of fibrin glue and that are relatively inexpensive.

In one aspect, the present disclosure relates to a synthetic polymer based adhesive formulation that comprises a discrete acid solution and a discrete base solution that when combined together form an adhesive that has properties substantially simulating selected properties of fibrin glue. The acid component includes a polymer and a cross-linking agent precursor and the base component includes a polymer and a base.

In another aspect, the disclosure herein relates to a delivery system for delivering and forming a synthetic polymer based adhesive. The delivery system includes a delivery device having a housing defining a first chamber and a second chamber. The first chamber has an acid solution contained therein wherein the acid solution includes a polymer and a cross-linking agent precursor. The second chamber has a base solution contained therein wherein the base solution includes a polymer and a base.

In another aspect, the disclosure herein relates to a method of making a synthetic polymer adhesive having properties that substantially resemble selected properties of fibrin glue. The method includes combining an acid solution with a base solution to form a synthetic polymer adhesive that has properties which substantially resemble selected properties of fibrin glue. The acid solution includes a polymer and a cross-linking agent precursor, and the base solution includes a polymer and a base.

In yet another aspect, the present disclosure relates to a method of simulating a medical procedure. The method includes combining an acid solution, which includes a polymer and a cross-linking agent precursor, with a base solution, which includes a polymer and a base. The combination of the solutions forms an adhesive that has properties substantially similar to that of fibrin glue. The method includes employing the synthetic polymer adhesive to simulate a medical procedure.

BRIEF DESCRIPTION OF THE FIGURES

In the course of this description, reference will be made to the accompanying drawing(s), wherein:

FIG. 1 is a cross-sectional view of one embodiment of a delivery system for providing and delivering a synthetic polymer adhesive.

DETAILED DESCRIPTION

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

The present disclosure is related to synthetic polymer based adhesives that, among other things, have properties which substantially resemble or simulate selected properties of fibrin glues, and that may be used in place of fibrin glue in simulated or training medical procedures. The synthetic polymer adhesive may be substantially similar to fibrin glue in one or more of its properties including, without limitation, tack, viscosity, consistency, set-times, and clarity. One advantage of employing the synthetic polymer adhesives described herein in simulated medical procedures is that they are relatively inexpensive as compared to the actual fibrin glues used in such procedures. Thus, the synthetic adhesives described herein substantially reduce the costs associated with the training and demonstration of simulated medical procedures that involve the use of fibrin adhesives while still providing a surgeon-in-training with a "real-life feel" of handling, applying and delivering a fibrin adhesive.

In one non-limiting example, the synthetic polymer adhesive disclosed herein may be used in place of fibrin glue in a simulation of a true tissue repair procedure as shown and described in co-owned U.S. patent application Ser. No. 12/101,553 filed Apr. 11, 2008 and published as U.S. Patent Publication No. 2009/0012629, which is hereby incorporated herein by reference. In the tissue repair procedure, fibrin glue is employed as a molded biocompatible carrier that is combined with and carries a biological agent, such as tissue particles, cells, collagen, etc. When demonstrating or simulating this tissue repair procedure, the synthetic polymer adhesive described herein may be used in place of actual fibrin glue.

The polymer adhesives described herein may have other applications as well. For instance, the adhesives may be used as a bone filler or bone filling material.

In one embodiment, the formulation of the synthetic polymer adhesive is provided as the combination of two discrete components—a discrete acid solution and a discrete base solution. As used herein, the term "discrete" is not intended to mean that the solutions have no components in common or that they are completely different from one another. In fact, as described below, the two solutions may have certain common components. Rather, the term "discrete" is used to mean that the two solutions are separate from one another and/or separately provided until combined during use to form the synthetic polymer adhesive.

The acid solution includes at least a polymer and a cross-linking agent precursor, and the base solution includes at least a polymer and a base. When the acid and base solutions are combined together, the cross-linking agent precursor forms a cross-linking agent that substantially cross-links the polymer(s) in the acid and base solutions to form a synthetic polymer adhesive that substantially simulates or otherwise resembles selected properties of fibrin glue. In one embodiment, the cross-linking agent precursor forms a cross-linking agent, which substantially crosslinks the polymer, only when the overall pH of the combined solutions is basic. The synthetic polymer adhesive formed may be a tacky, non-Newtonian fluid.

The properties of the synthetic polymer adhesive formulation may be modified to resemble one or more particular properties of specific fibrin glues by varying the polymers, cross-linking agent precursors, cross-linking agents, and bases. The properties also may be modified by varying the concentration of the polymers, cross-linking agent precursors, cross-ling agents, and bases. Additionally, the properties may be modified by varying the pH of either solution or of both solutions. The properties may further be modified by the addition of other compounds such as, for example, by the addition of other polymers and/or secondary solvents.

The Acid Component

As indicated above, the acid component of the formulation is provided as a solution that includes at least a polymer and a cross-linking agent precursor. The polymer may be an alcohol-group containing polymer, such as polyvinyl alcohol (PVA). The polymer also may be polyvinyl acetate (PVAc), polyhydroxymethylmethacrylate, poly(2-hydroxypropyl methacrylate), poly(2-ethyl-2-oxazoline), poly(acrylamide), poly(4-vinylpyridine), poly(acrylic acid), poly(ethylene glycol), poly(ethylene oxide), poly(methyacrylic acid), poly(n-vinylpyrrolidone), poly(n-iso-propylacrylamide), or any combination of the above. In one embodiment, the concentration of the polymer in the acid component may be between about 1% and about 15% by weight based on the total weight of the acid solution, more typically between about 2% and about 6% by weight based on the total weight of the acid solution. In one embodiment, the concentration of the polymer is about 3% to about 4% by weight based on the total weight of the acid solution.

The cross-linking agent precursor may be pH dependent and may form one or more pH dependent cross-linking agents after reaction with the base. Examples of such pH dependent cross-linking agents formed from the precursor after reaction with the base may be, but is not limited to, one or more of borates including alkaline metal borates, amine borates, and ammonium borates or one or more phosphates including alkaline metal phosphates, amine phosphates, and ammonium phosphates. For example, borates may include potassium metaborate, lithium metaborate, ammonium borate, calcium metaborate, sodium tetraborate, potassium tetraborate, sodium borate, methylammonium hydrogen tetraborate, and the like. For example, the phosphates may include potassium phosphate, calcium phosphate, and ammonium phosphate, and the like. The pre-cursor to the cross-linking agent (i.e., the crossing linking agent precursor) may be the acid form of the corresponding cross-linking agent and may include multivalent acids including boric acid, metaboric acid, tetraboric or pyroboric acid, phosphoric acid, metaphosphoric acid, colamine phosphoric acid, phosphoric acid tridecyl ester, and the like. In one embodiment, the concentration of the cross-linking agent precursor may be between about 0.10% and about 3.0% by weight and more typically between about 0.10% and about 1.0%, and preferably between about 0.10% and 0.20% by weight, based on the total weight of the acid solution. In one, specific, non-limiting example, the concentration of the cross-linking agent precursor is about 0.10% to about 0.15% by weight based on the total weight of the acid solution. The ranges of concentrations and the specific concentrations of the polymer and the cross-linking agent precursor also may be lower or higher depending on such factors as, for example, the particular application, the desired characteristics of the resulting adhesive, and the solubility of the polymers and cross-linking agent precursors. Preferably, the polymer of the acid solution, such as but not limited to polyvinyl alcohol, acts as a viscosity modifier.

The Base Component

As indicated above, the base component of the formulation is provided as a solution that includes at least a polymer and a base. Similar to the acid solution, the polymer may be one or more of the above-listed polymers including without limitation, polyvinyl alcohol and polyvinyl acetate. Other polymers may include water-soluble polymers such as polyhydroxymethylmethacrylate, poly(2-hydroxypropyl methacrylate), poly(2-ethyl-2-oxazoline), poly(acrylamide), poly(4-vinylpyridine), poly(acrylic acid) sodium salt, poly(ethylene glycol), poly(ethylene oxide), poly(methyacrylic acid) sodium salt, poly(n-vinylpyrrolidone), poly(n-iso-propylacrylamide) or any combination of the above mentioned polymers. It is preferable that one polymer component in either the acid or the base solution contain functionality allowing for crosslinking which may include alcohol, carboxylic acid, phosphoric acid, boric acid, amines, amides, and acids/bases therefrom. Preferably, one of the polymer components contains an alcohol functionality. In one embodiment, the concentration of the polymer in the base solution may be between about 2% and about 15% by weight and more typically between about 2% and about 7% by weight based on the total weight of the base solution. In one, specific, non-limiting example, the concentration of the polymer is about 3% to about 4% by weight based on the total weight of the base solution.

The base may be any commonly known base, such as sodium hydroxide, potassium hydroxide, triethylamine, ethylamine, ammonium hydroxide, sodium bicarbonate, sodium carbonate, etc. In one embodiment, the concentration of the base may be between about 0.15% and about 0.75% by weight based on total weight of the base solution. The concentration of the base also may be dependent on the chemistry of the cross-linking precursor. In another embodiment, the concentration is about 0.20% by weight based on the total weight of the base solution. The concentrations of the polymer and the base also may be lower or higher depending on such factors as, for example, the particular application, the desired characteristics of the resulting adhesive, and the solubility of the polymers and base. Preferably, the polymer of the acid component, such as but not limited to polyvinyl alcohol, acts as a thickening agent.

Other Additives

Additional additives also may be included in the acid and base solutions. For example, secondary solvents, such as dimethyl sulfoxide (DMSO), may be added to either solution to increase the solubility of the polymer. Additionally, stabilizers, preservatives, fungicides and/or bactericides also may be added to either or both solution(s) to stabilize and preserve the solutions and to extend their shelf lives. Further, tackifiers, such as polyacrylic acid (preferably, polyacrylic acid having a molecular weight between about 2000 and about 750,000) and poly[bis(2-chloroethyl)ether-alt-1,3-bis[3-dimethylamino)propyl]urea], quaternized (polyquaternium-2), poly(methacrylic acid), poly(vinyl phosphoric acid), poly(2-hydroxyethyl methacrylate-co-methacrylic acid), or poly(maleic acid) and the like may be added to either of the acid or base solutions in order to enhance the tack of the resultant synthetic polymer adhesive formulation. Other compounds such as polyethylene glycol between about 200 MW to 6000 MW also may be added to the acid and base solutions as well to change dough time, set time, work time, and final stiffness of the resulting product.

As mentioned above, the polymer adhesive described herein may be used for applications other than simulating the properties of fibrin glue. In one such application, the adhesive may be used as or simulate a bone filler or bone filling material. When used as such, the base in the base solution may be calcium hydroxide, and phosphoric acid, poly(vinyl phosphoric acid), and the like may be an additional acid added to the acid solution.

Adhesive Formulation and Delivery

In one embodiment of a combination of the discrete acid and base solutions that result in the formulation discussed herein, the acid solution includes about 2% to about 15% polyvinyl alcohol by weight based on total weight of the solution, and a cross-linking agent precursor that does not substantially form a cross-linking agent while in the acidic solution. One such cross-linking agent precursor is boric acid. When boric acid is used, the concentration of boric acid may be between about 0.1% and about 0.56% by weight based on total weight of the acid solution. To keep the boric acid from substantially forming a cross-linking agent that crosslinks the polyvinyl alcohol, the pH of the acid solution is preferably no greater than 6.5. Although it will be understood that some cross-linking agents may form and some crosslinking may occur even though the solution is acidic.

The viscosity of the acid solution can be varied by varying the pH or neutralizing the acid so that some of the cross-linking agent precursor forms the cross-linking agent to result in some crosslinking of the polymer in the acid solution. A lower pH results in a lower amount of crosslinking and a lower viscosity of the acid solution. A higher pH results in a greater amount of crosslinking and a higher viscosity of the acid solution.

The base solution of the adhesive formulation includes about 2% to about 15% of polyvinyl alcohol by weight and about 0.2% to about 0.75% by weight of sodium hydroxide, each based on the total weight of the base solution. The concentration of the sodium hydroxide should be such so that when the two solutions are combined, the resulting combination has a pH of above about 7 so as to initiate the cross-linking agent precursor to form the crosslinking agent which crosslinks the polyvinyl alcohol.

The synthetic polymer adhesive described herein may be applied and delivered in substantially the same manner and with substantially the same devices that are used to apply and deliver actual fibrin glue. In other words the discrete acid and base solutions of the formulation described herein may be applied, combined and delivered in a manner substantially similar to that of the fibrinogen and thrombin components of fibrin glue.

FIG. 1 illustrates one embodiment of a delivery system 10 that may be used for storing and delivering a synthetic polymer adhesive formulation. The delivery system 10 includes a delivery device 12, such as the illustrated double barrel syringe. Delivery device 12 includes a housing 14 that defines a first discrete compartment 16 and a second discrete compartment 18. The acid solution 20 of the adhesive formulation is contained and/or provided within the first compartment 16, and the base solution 22 of the adhesive formulation is contained and/or provided within the second compartment 18. Device 12 also includes dispensing orifices 24 and 26 in flow communication with the first and second compartments 16 and 18, respectively. Plungers 28 and 30 are disposed and moveable within first and second compartments 16 and 18, respectively, to force the acid and base solutions 20 and 22 out of the compartments through the dispensing orifices 24 and 26. To provide the desired mixing, the solutions 20 and 22 are dispensed from orifices 24 and 26 to locations that are preferably substantially adjacent to one another. For example, the solutions 20 and 22 may be dispensed into mixing zone 32 wherein the solutions are combined to form a synthetic polymer adhesive. In the embodiment shown, the solutions are combined without the use of a mixing tip. However, a mixing tip also may be employed to mix the solutions.

The diameter or size of the dispensing orifice 24 and 26 can affect the reaction time of the crosslinking, and thus, affect the set-times of the resulting adhesive. For example, a smaller sized bore decreases the reaction time of the crosslinking, and thus, decreases the time it takes for the adhesive to set, i.e., the adhesive will set faster. Conversely, a larger sized bore increases the reaction time of the crosslinking, and thus, increases the time it takes for the adhesive to set, i.e., the adhesive will set slower.

Other devices and methods also may be used to contain the components of and deliver the adhesive formulation. For example, the adhesive formulation may be delivered by two separate syringes, wherein each syringe contains one of the solutions. It is preferred that the compartments or chambers containing the acid and base components be isolated from one another and that no unintended mixing occurs within the dispensing device.

Example 1

A formulation of a synthetic polymer adhesive of the present disclosure was prepared as described below.

The acid solution of the synthetic polymer adhesive formulation was prepared in the following manner. A 3.85 wt. % solution of boric acid was prepared by dissolving boric acid in water. 300 ml of 4 wt. % of polyvinyl alcohol solution (The Science Shop, Santa Clara, Calif., Part No. SJS-C6191) was placed in a 400 ml beaker. Approximately 10.5 ml of the boric acid solution was added dropwise to the 4 wt. % polyvinyl alcohol solution until the solution included about 3.86 wt. % of polyvinyl alcohol, about 0.13 wt. % of boric acid and about 96.01 wt. % water, each being based on the total weight of the acid solution. The solution was heated to between about 60 degrees Celsius and about 80 degrees Celsius with constant stirring until the solution was transparent.

The base solution of the synthetic polymer adhesive formulation was prepared in the following manner. Approximately 300 ml of the 4 wt. % polyvinyl alcohol solution was placed in a 400 ml beaker. Approximately 0.6166 grams of sodium hydroxide was added to the 4 wt. % polyvinyl alcohol solution until the solution included about 3.99 wt. % of polyvinyl alcohol, about 0.20 wt. % sodium hydroxide and about 96.01 wt. % of water, each being based on the total weight of the base solution. The solution was heated to between about 60 degrees Celsius and about 80 degrees Celsius until uniform and the sodium hydroxide was completely dissolved.

Fifty 8 ml manual dispensing double barrel syringes (Global Tech, Lake Worth, Fla., Part No. 65002) were filled with the acid and base solutions. The acid and the base solutions were then dispensed from the syringes and combined to form a synthetic polymer adhesive. The adhesive was found to have substantially similar viscosity, consistency, set-time, tack, and clarity as fibrin glue.

Example 2

A synthetic polymer adhesive formulation was prepared as described below.

An acid solution was prepared in the following manner. A 3.85 wt. % boric acid solution was prepared as described in Example 1. Next, polyethylene glycol 400 was dissolved in a 4 wt. % polyvinyl alcohol solution and the boric acid solution was added dropwise so as to form a solution that has about 3.81 wt. % polyvinyl alcohol, about 0.11 wt. % boric acid, about 1.90 wt. % PEG 400 and about 94.18 wt. % water, each being based on the total weight of the acid solution. The solution was heated to between about 60 degrees Celsius and about 80 degrees Celsius and was stirred until uniform.

A base solution was prepared in the same manner as described in Example 1. The acid and base solutions were then combined in the manner described in Example 1 to form a polymer adhesive.

Example 3

A synthetic polymer adhesive formulation was prepared as described below.

An acid solution was prepared in the following manner. A 3.85 wt. % boric acid solution was prepared as described in Example 1. Next, DMSO was added to a 4 wt. % polyvinyl alcohol solution and the boric acid solution was added dropwise so as to form a solution that has about 3.20 wt. % polyvinyl alcohol, about 0.46 wt. % boric acid, about 8.0 wt. % DMSO and about 88.34 wt. % water, each being based on the total weight of the acid solution. The solution was heated to between about 60 degrees Celsius and about 80 degrees Celsius and was stirred until uniform.

The base solution was prepared by adding DMSO and sodium hydroxide to a 4 wt. % polyvinyl alcohol solution so as to form a solution that has about 3.59 wt. % polyvinyl alcohol, about 8.97 wt. % DMSO, about 0.67 wt. % sodium hydroxide and about 86.77 wt. % water, each being based on the total weight of the base solution. The solution was heated to between about 60 degrees Celsius and about 80 degrees Celsius until uniform and the sodium hydroxide is completely dissolved.

The acid and base solutions were then combined in the manner described in Example 1 to form a polymer adhesive.

Example 4

A synthetic polymer adhesive formulation was prepared as described below.

A boric acid solution and acid solution were prepared in the same manner as described in Example 3, except that the acid solution was prepared so that it contains about 3.08 wt. % polyvinyl alcohol, about 0.59 wt. % boric acid, about 7.69 wt. % DMSO and about 88.64 wt. % water, each being based on the total weight of the acid solution.

A base solution was prepared in the same manner as described in Example 3, except that the base solution was prepared so that is contains about 3.57% polyvinyl alcohol, about 8.93% DMSO, about 0.89% sodium hydroxide and about 86.61% water, each being based on the total weight of the base solution.

The acid and base solutions were then combined in the manner described in Example 1 to form a polymer adhesive.

Example 5

A synthetic polymer adhesive formulation was prepared as described below.

A boric acid solution and acid solution were prepared in the same manner as described in Example 3, except that the acid solution was prepared so that it contains about 3.33% polyvinyl alcohol, about 0.32% boric acid, about 8.33% DMSO and about 88.01% water, each being based on the total weight of the acid solution.

A base solution was prepared in the same manner as described in Example 3, except that the base solution was prepared so that is contains about 3.56% polyvinyl alcohol, about 8.89% DMSO, about 1.11% sodium hydroxide and about 86.44% water, each being based on the total weight of the base solution.

The acid and base solutions were then combined in the manner described in Example 1 to form a polymer adhesive.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein. Thus, for example, while the methods and systems discussed above have been described in the context of a fibrin-like synthetic adhesive formulation that finds particular application in the training of surgeons handling fibrin, the formulations and methods of making and delivering such formulations may also have other applications and uses. For example synthetic corneal lenses; breast implants; cosmetic epidermal injection for wrinkle removal, fill the lips, or provide fullness to other areas; drug delivery system; wound care; or topical usages.

What is claimed is:
1. A system of discrete compositions mixable in approximately equal quantities to form a synthetic polymer-based adhesive formulation that has properties substantially simulating one or more properties of fibrin glue selected from tack, viscosity, consistency, set-times, and clarity, the system of discrete compositions comprising:

a discrete acid solution comprising about 2 wt % to about 15 wt % polyvinyl alcohol and about 0.1 wt % to about 0.5 wt % boric acid, the discrete acid solution having a pH of no greater than about 6.5; and a discrete base solution comprising about 0.2 wt % to about 0.75 wt % sodium hydroxide and about 2 wt % to about 15 wt % polyvinyl alcohol, the discrete base solution having a pH of between about 7.0 to about 14.0.

2. The system of claim 1 wherein at least one of the acid solution and the base solution further comprises one or more of polyvinyl acetate, polyhydroxymethylmethacrylate, poly(2-hydroxypropyl methacrylate), poly(2-ethyl-2-oxazoline), poly(acrylamide), poly(4-vinylpyridine), poly(ethylene glycol), poly(ethylene oxide), poly(methacrylic acid), poly(methacrylic acid) sodium salt, poly(acrylic acid) sodium salt, poly(n-vinylpyrrolidone), and poly(n-iso-propylacrylamide).

3. The system of claim 1 in which the discrete acid solution further comprises a cross-linking agent precursor chosen from metaboric acid, tetraboric acid, pyroboric acid, phosphoric acid, metaphosphoric acid, colamine phosphoric acid, phosphoric acid tridecyl ester, and combinations thereof.

4. The system of claim 1 wherein at least one of the acid and base solutions comprises one or more of a stabilizer and a preservative.

5. The system of claim 1 wherein at least one of the acid and base solutions comprises a secondary solvent.

6. The system of claim 5 wherein the secondary solvent is dimethyl sulfoxide.

7. The system of claim 1 wherein at least one of the discrete acid solution and the discrete base solution further comprises a compound that enhances the tack of a synthetic adhesive formed from a combination of the acid and base solutions.

8. The system of claim 7 in which the compound comprises polyacrylic acid.

9. The system of claim 1 in which the discrete base solution further comprises at least one of potassium hydroxide, triethylamine, ethylamine, ammonium hydroxide, sodium bicarbonate, and sodium carbonate.

10. A combination of a delivery device and a synthetic polymer adhesive, comprising:

a delivery device having a housing defining a first chamber and a second chamber;

a discrete acid solution contained within the first chamber, the acid solution comprising about 2 wt % to about 15 wt % polyvinyl alcohol and about 0.1 to about 0.5 wt % boric acid, the discrete acid solution having a pH of no greater than about 6.5;

a discrete base solution contained within the second chamber, the base solution comprising about 0.2 wt % to about 0.75 wt % sodium hydroxide and about 2 wt % to about 15 wt % polyvinyl alcohol, the discrete base solution having a pH of between about 7.0 to about 14.0;

a first dispensing orifice in flow communication with the first chamber for dispensing the first fluid therefrom; and a second dispensing orifice in flow communication with the second chamber for dispensing the second fluid therefrom, wherein the synthetic polymer adhesive comprises the discrete acid solution and the discrete base solution.

11. The combination of claim 10 in which the chambers are isolated from each other and said orifices are isolated from each other.

* * * * *